United States Patent
Saab

(10) Patent No.: US 6,905,510 B2
(45) Date of Patent: Jun. 14, 2005

(54) HEAT TRANSFER CATHETERS AND METHODS OF MAKING AND USING SAME

(76) Inventor: Mark A. Saab, 396 Andover St., Lowell, MA (US) 01852

(*) Notice: Subject to any disclaimer, the term of this patent is extended or adjusted under 35 U.S.C. 154(b) by 194 days.

(21) Appl. No.: 10/184,889

(22) Filed: Jul. 1, 2002

(65) Prior Publication Data

US 2002/0177804 A1 Nov. 28, 2002

Related U.S. Application Data

(63) Continuation of application No. 09/309,052, filed on May 10, 1999, now Pat. No. 6,440,158, which is a division of application No. 08/453,066, filed on May 26, 1995, now Pat. No. 5,902,268, which is a division of application No. 08/287,114, filed on Aug. 8, 1994, now Pat. No. 5,624,392, which is a continuation-in-part of application No. 07/929,305, filed on Aug. 13, 1992, now Pat. No. 5,342,301.

(51) Int. Cl.[7] .................................................. A61F 7/00
(52) U.S. Cl. ............................ 607/105; 606/21; 606/28
(58) Field of Search ............. 606/21–31; 607/101–105; 604/21

(56) References Cited

U.S. PATENT DOCUMENTS

| 4,762,130 A | * | 8/1988 | Fogarty et al. ............. 606/159 |
| 4,900,314 A | * | 2/1990 | Quackenbush ............. 604/527 |
| 5,181,911 A | | 1/1993 | Shturman |
| 5,190,540 A | * | 3/1993 | Lee ............................. 606/28 |
| 5,226,888 A | | 7/1993 | Arney |
| 5,308,356 A | | 5/1994 | Blackshear, Jr. et al. |
| 5,383,856 A | | 1/1995 | Bersin |
| 5,554,119 A | | 9/1996 | Harrison et al. |

* cited by examiner

Primary Examiner—Michael Peffley
(74) Attorney, Agent, or Firm—Oblon, Spivak, McClelland, Maier & Neustadt, P.C.

(57) ABSTRACT

Heat transfer catheter apparatus and methods of making and using same are disclosed wherein a fluid connection is provided between the distal portions of two adjacent, thin-walled, high strength fluid lumens to define a closed loop fluid circulation system capable of controlled delivery of thermal energy to or withdrawal of thermal energy from remote internal body locations.

10 Claims, 4 Drawing Sheets

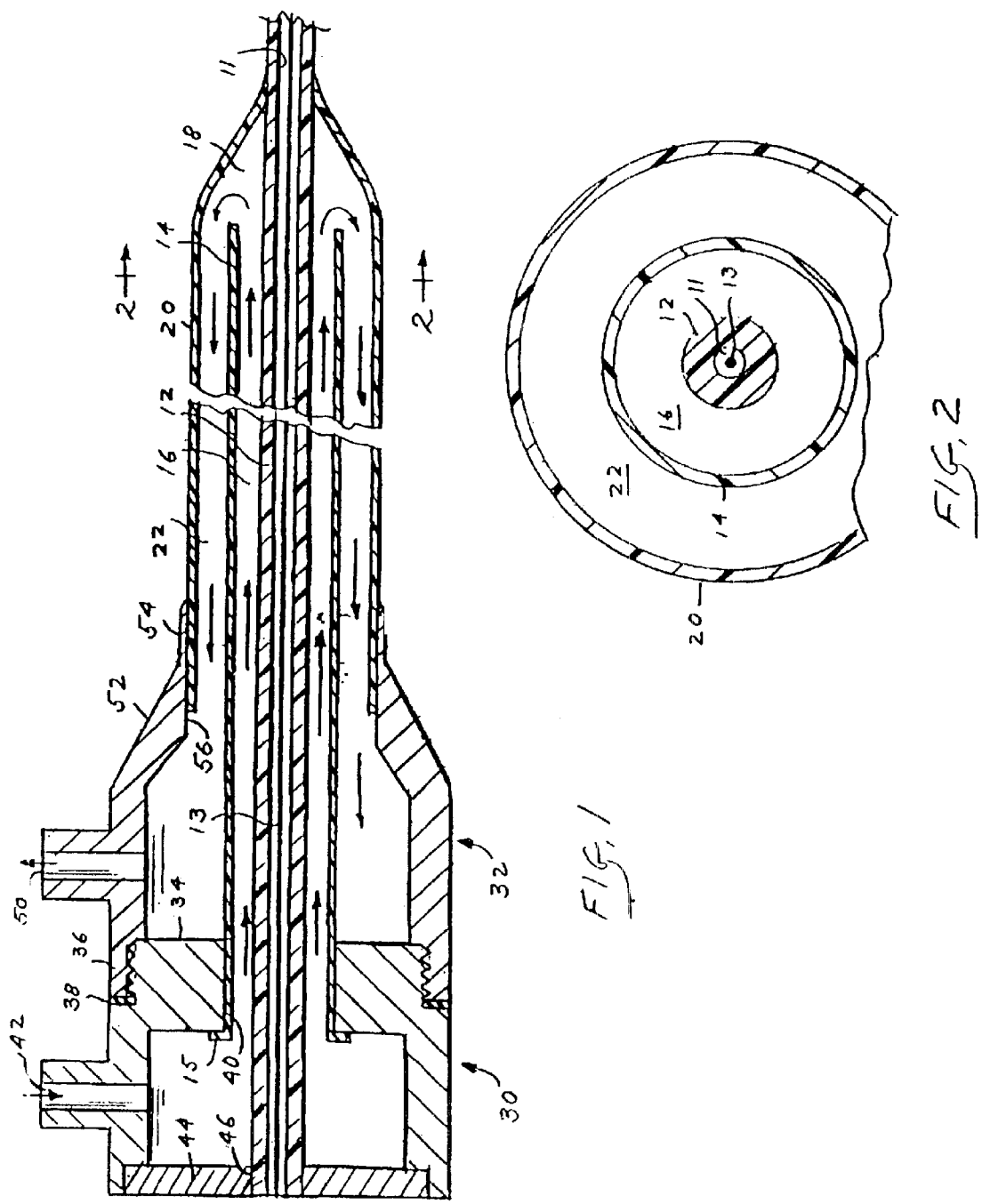

HEAT TRANSFER CATHETERS AND METHODS OF MAKING AND USING SAME

CROSS-REFERENCE TO RELATED APPLICATIONS

This application is a continuation of U.S. patent application Ser. No. 09/309,052, filed May 10, 1999, now U.S. Pat. No. 6,440,158 which is a division of U.S. patent application Ser. No. 08/453,066, filed May 26, 1995, now U.S. Pat. No. 5,902,268, issued May 11, 1999; which in turn was a division of U.S. patent application Ser. No. 08/287,114, filed Aug. 8, 1994, now U.S. Pat. No. 5,624,392, issued Apr. 29, 1997; which was in turn a continuation-in-part of U.S. patent application Ser. No. 07/929,305, filed Aug. 13, 1992, now U.S. Pat. No. 5,342,301, issued Aug. 30, 1994. The disclosures of these patents and patent applications are incorporated herein by reference.

BACKGROUND OF THE INVENTION

The present invention relates generally to heat transfer catheter apparatus for internal body applications, and more particularly, to catheters adapted for delivering heat transfer fluids at temperatures above or below normal body temperatures to selected internal body sites that are relatively remote from the point of entry into the body for specialized medical applications. The heat transfer catheters of this invention may, in one embodiment, comprise fluid lumens that have very thin-walled, high strength sidewalls that are substantially inelastic. In an alternative embodiment, the fluid lumen sidewalls may be elastomeric. In either case, the fluid lumens are readily inflatable under fluid pressure and readily collapsible under vacuum. The heat transfer catheter apparatus of this invention may comprise multi-lumen units having two or more lumens. The heat transfer catheter apparatus of this invention may also, in different embodiments, be used alone or in conjunction with other medical apparatus. The heat transfer catheter apparatus of this invention may also, in different embodiments, comprise single or multi-lumen dilatation balloons.

It is well known in the art to prepare and use catheters for a variety of medical applications. In one familiar application, inexpensive, disposable catheters having one open end and one closed end are utilized as protective sheaths for various medical instruments. The use of such elongated, tubular sleeves as protective sheaths can minimize the costs and problems associated with cleaning and sterilizing medical instruments, such as endoscopes, between uses. In the case of medical optical instruments, such as endoscopes, the protective sleeves may include a "window" portion designed to align during use with the optical portion of the medical instrument.

Typical of the prior art in this field are U.S. Pat. Nos. 4,646,722 (Silverstein et al.) and U.S. Pat. No. 4,907,395 (Opie et al.). The Silverstein et al. patent teaches the use of an endoscope sheath comprising a flexible tube surrounding the elongated core of an endoscope. The flexible tube has a transparent window near its distal end positioned in front of the viewing window of the endoscope. An alternative embodiment of the Silverstein et al. sheath for use with side-viewing endoscopes is shown in FIG. 10 of that patent. In this embodiment, the sheath 110 comprises an end cap 112 of relatively rigid material mounted at the end of a flexible cylindrical tube of elastomeric material 114 formed into a roll 116. The end cap 112 includes a pair of transparent windows 118, 120. The later Opie et al. patent is essentially an improvement invention directed to a method of packaging and installing the endoscope sheaths of the Silverstein et al. patent.

U.S. Pat. Nos. 3,794,091 (Ersek et al.) and U.S. Pat. No. 3,809,072 (Ersek et al.) are directed to sterile sheaths for enclosing surgical illuminating lamp structures that have elongated light transmitting shafts. The sheaths in Ersek et al. are fabricated from films of flexible plastic material, such as vinyl tubing, polyethylene or polypropylene. Ersek et al. prefer a wall thickness of between three and six mils for the required durability, rigidity and transparency. The tip end portion 20 of the sheath is described as a "generally rigid lens element" sealed to the sheath in a continuous sealing line 21 by thermal welding or adhesive bonding.

U.S. Pat. No. 4,957,112 (Yokoi et al.) describes an ultrasonic diagnostic apparatus, the distal end portion of which includes a cover 24 made of a thin, hard, polyethylene sheet that has a window portion 34 along a sidewall. U.S. Pat. No. 4,878,485 (Adair) describes a rigid, heat sterilizable sheath S that provides an outer casing for a video endoscope. The sheath includes a viewing window 32, a flat disc positioned at the distal end in the optical path of the endoscope. U.S. Pat. No. 4,819,620 (Okutsu) describes an endoscope guide pipe which is rigid and formed from a transparent material such as glass or plastic. In one embodiment shown in FIG. 6 of that patent, a pair of slots in the sidewall of the guide pipe is filled with a transparent material, such as glass, to define a window section 12f. U.S. Pat. No. 4,470,407 (Hussein) describes a flexible, elongated tube with an elastomeric balloon sealingly mounted at the distal end of the tube for enclosing an endoscope. Inside the body, the balloon can be inflated to facilitate endoscope viewing. U.S. Pat. No. 4,201,199 (Smith) describes a relatively thick, rigid glass or plastic tube 10 which fits over an endoscope. The distal end of the tube in the Smith patent is provided with an enlarged, sealed bulb 12 having a radius of at least 3–4 mm to reduce optical distortion caused by a too-small radius of curvature. U.S. Pat. No. 3,162,190 (Del Gizzo) describes a tube 19, made from molded latex or similar material, through which an optical instrument is inserted. Viewing is through an inflatable balloon element 24 mounted at the distal end of the tube. U.S. Pat. No. 3,698,791 (Walchle et al.) describes a very thin, transparent microscope drape which includes a separately formed, optically transparent, distortion-free lens for viewing.

In another familiar application, multi-lumen balloon catheters are utilized as dilatation devices for dilating a blood vessel, e.g. a coronary artery, or other body canal. The use and construction of balloon catheters is well known in the medical art, as described for example in U.S. Pat. No. Re. 32,983 (Levy) and U.S. Pat. No. 4,820,349 (Saab). Other patents generally showing the application of various types of balloon catheters include U.S. Pat. No. 4,540,404 (Wolvek), U.S. Pat. No. 4,422,447 (Schiff), and U.S. Pat. No. 4,681,092 (Cho et al.).

It is also well known in the medical art to employ catheters having shafts formed with a plurality of lumens in instances where it is necessary or desirable to access the distal end of the catheter or a particular internal body location simultaneously through two or more physically separate passageways. For example, U.S. Pat. No. 4,576,772 (Carpenter) is directed to increasing the flexibility or articulatability of a catheter having a shaft formed with a plurality of lumens that provide distinct conduits for articulating wires, glass fiber bundles, irrigation, and vacuum means.

It is also known, as shown in U.S. Pat. No. 4,299,226 (Banka) and U.S. Pat. No. 4,869,263 (Segal et al.), to employ multi-lumen catheters with a balloon. The Banka patent shows a double-lumen catheter shaft of coaxial construction wherein the outer lumen carries saline solution to inflate a balloon, and an inner lumen, located coaxially inside the outer lumen, is adapted to receive a stylet or guide wire. In the Banka patent, the double-lumen dilatation catheter is designed to be coaxially contained within the single lumen of a larger diameter guide catheter. In the Banka device, each of the three coaxial lumens is a separate, distinct passageway without any means for fluid passage between two of those lumens. Such fluid passage between lumens could occur only accidentally in the event of a rupture of one of the lumens, and such results are clearly contrary to the intent of that patent.

The Segal et al. patent shows a more complex dilatation catheter apparatus having five separate, non-coaxial lumens (FIGS. 1 and 2 of that patent) extending through the catheter, including a balloon inflation lumen 18, a distal lumen 17, a wire lumen 22, a pulmonary artery lumen 26, and a right ventricular lumen 28. Lumens 17 and 18 extend the entire length of the catheter from the proximal extremity to the distal extremity. Lumen 17 exists through the distal extremity 14b of the catheter. The distal extremity of lumen 18 is in communication with the interior of balloon 16 to permit inflation and deflation. Lumens 22, 26 and 28, on the other hand, only pass partly or completely through the larger diameter, proximal portion 14a of the catheter. The Segal et al. catheter apparatus is prepared by extrusion (col. 2, lines 53 and 54). Multi-lumen catheters in conjunction with a balloon or inflatable element have also been adapted for a variety of special usages. U.S. Pat. Nos. 4,994,033 (Shockey et al.) and U.S. Pat. No. 5,049,132 (Shaffer et al.) are both directed to balloon catheters adapted for intravascular drug delivery. Both of these patents employ a similar concentric, coaxial, double balloon construction surrounding a central lumen. The larger, outer balloons in both cases include a set of apertures for the delivery of medication to surrounding tissue when the catheter is in place. No fluid connection or passageway is provided between the inner and the outer balloons or the lumens serving those balloons in these patents.

U.S. Pat. No. 4,681,564 (Landreneau) teaches another type of multi-lumen catheter in conjunction with a balloon element. In this patent, a first fluid passage is in communication with the balloon element so as to selectively inflate or deflate it; a second, separate fluid passage has outlet openings at its distal end for purposes of delivering medication or other treating fluid to the body space; and, a third, separate passage has drain openings communicating with the body space so as to drain excess fluids. This patent thus describes a catheter loop whereby treating fluid enters the body through a first lumen and some portion of that fluid leaves the body through a separate second lumen. But, this is clearly not a closed loop in the sense that some portion of the treating fluid remains in the body, and all of the treating fluid must pass through a portion of the human body on its way from the inlet lumen to the drainage passage. Such treating fluid certainly could not contain toxic substances which would poison or harm the body.

U.S. Pat. No. 4,581,017 (Sahota) and U.S. Pat. No. 5,108,370 (Walinsky) are both directed to perfusion balloon catheters designed to maintain blood flow through a blood vessel during a dilatation procedure, for example an angioplasty. In Sahota, a hollow, central shaft passes through the interior of the balloon element, and apertures in the side wall of the catheter shaft upstream and downstream from the balloon permit blood to flow into the shaft, past the balloon, and back into the blood vessel. A small, separate tube connected to the balloon is used to inflate and deflate the balloon. No fluid connection is provided between the balloon and the central shaft. A generally similar balloon catheter construction is described in Walinsky.

U.S. Pat. No. 4,299,237 (Foti) is directed to an apparatus for transferring thermal energy from a calorized fluid to an ear canal and tympanic membrane. In one embodiment, this apparatus comprises a rigid structure made of a semi-rigid material and pre-shaped so as to conform to the internal geometry of an ear canal. Rigid internal struts keep open a fluid circulation loop served by a fluid inlet tube and a fluid outlet tube. In an alternative embodiment, the Foti apparatus comprises an inflatable balloon element surrounding a hollow, central shaft containing a depth indicator for proper positioning of the device. The balloon element is inflated and deflated through separate fluid inlet and outlet tubes connected through a rigid ear mold adjoining the balloon element. The Foti apparatus in either embodiment is relatively short (typically about 32 mm in length) and relatively wide (overall diameter of about 6 mm), therefore bearing little resemblance to a vascular-type catheter which is typically several hundred millimeters in length but with a diameter of only about three–four millimeters or less. Furthermore, the Foti device is designed to operate only at a relatively low fluid pressure because it is not intended for dilating internal body canals and also because there is no need to force fluid through a very small diameter conduit over relatively long distances, again in contrast to a vascular-type dilatation catheter.

In the above-cited prior art, which is incorporated herein by reference, it should be understood that the term "multi-lumen" in the phrase "multi-lumen balloon catheters" typically means that the catheter shaft is multi-lumen (as opposed to the balloon segment in communication with the catheter shaft). By contrast, my U.S. Pat. No. 5,342,301, of which this application is a continuation-in-part, is directed to novel multi-lumen balloons. The multi-lumen balloons of my aforementioned invention are distinguished from the multi-lumen balloon catheters of the prior art, as discussed above, in that the walls defining the lumens are formed as an integral part of the balloon. The terms "integral part" and "integrally formed" as used in U.S. Pat. No. 5,342,301 each mean that at least a lumen of the multi-lumen balloon shares a common wall portion with part of at least one inflatable balloon segment. By contrast, the prior art shows lumens that are formed as a part of a conventional catheter shaft and are defined by the relatively thick walls of that catheter (e.g., Segal et al.), catheter lumens that communicate with or terminate in a balloon segment (e.g., Banka and Segal et al.), and lumens in a shaft that passes coaxially through a balloon segment (e.g., Banka, Sahota, and Walinsky).

In many conventional and non-conventional medical catheter applications, it would be desirable to provide a means for continuously transferring over an extended time period controlled amounts of thermal energy to or away from one or more adjacent locations along or at the distal end of an elongated, vascular-type catheter. Heat transfer can be effected, of course, by circulating a heat transfer fluid inside a catheter lumen. This straightforward approach is complicated, however, by enormous and heretofore unsurmountable physical limitations and obstacles.

Thus, a single lumen catheter can certainly deliver a heat transfer fluid to the closed distal end of the catheter. But, if the heat transfer fluid is at a temperature different from body temperature, the result of this procedure would be to merely create a temporary temperature gradient along the length of the catheter. At locations distal from the point where the fluid was introduced to the catheter, the temperature of the fluid in the catheter would tend to approach the internal body temperature. Furthermore, even this temperature effect would exist for only a relatively short time until the fluid at every point along the catheter gradually heated or cooled to body temperature. Clearly, this approach cannot be used to continually transfer controlled amounts of thermal energy to or away from internal body locations over an extended time period.

To effect continuous, controlled transfer of thermal energy to or from a body location adjacent the catheter therefore requires, at a minimum, a two-lumen catheter construction. With such a two-lumen construction, a continuous flow of heat transfer fluid can, at least in theory, be established. Fresh fluid at any desired temperature can be continuously introduced at the proximal end of a first or inlet catheter lumen and passed through that first lumen to a distal location inside the body, then passed through fluid connection means directly to the second or outlet catheter lumen, and finally passed back along that second lumen to be withdrawn at the proximal end as spent fluid for discarding or recycling. If the continuous fluid flow rate through such a two-lumen catheter system is sufficiently rapid, this construction makes it possible to establish and substantially maintain a fluid temperature inside the catheter that is above or below normal body temperature at any location along the length of the catheter. Correspondingly, if the catheter is constructed of a material which has good heat transfer properties and which is also sufficiently flexible so as to closely conform to the surrounding body cavity, the temperature of the fluid inside the catheter can be transferred to adjacent portions of the body that are in contact with or in proximity to the catheter sidewalls.

There are problems, however, associated with a two-lumen catheter configuration for carrying heat transfer fluid. A principal problem with such a configuration, utilizing conventional catheter and balloon construction and materials, relates to the size of the final apparatus. It will be apparent to those skilled in the art that catheter constructions intended for blood vessels and similar very small diameter body passages must be of correspondingly small diameter. This size problem is exacerbated by a two-lumen catheter construction, whether the lumens are configured side-by-side or concentrically. In either case, a significant proportion of the limited space inside the blood vessel or other body passage is occupied by relatively thick catheter sidewalls leaving relatively little open cross-sectional area for circulating fluids or as passageways for medical instruments and the like.

For example, the relatively thick sidewalls that define the lumens of conventional multi-lumen catheters, such as in the prior art patents cited above, typically range from about 0.003 to about 0.010 inches or greater. In part, the reason that conventional multi-lumen catheters have utilized such thick sidewalls is because these devices are fabricated from materials that are not high in tensile strength. Most balloon catheter shafts have conventionally been made by extrusion of a thermoplastic material. The resulting shafts are typically not substantially oriented, therefore not high tensile strength. Because rupture of one of these catheters while in use might cause air bubbles or dangerous fluids to leak into the blood stream resulting in death or serious injury, the catheter sidewalls had to be made thick enough to insure safety and reliability. This was especially important where the catheter was intended to carry fluid under pressure. Furthermore, such thick-walled catheter lumens are not readily inflatable under fluid pressure nor readily collapsible under vacuum, thereby complicating the process of inserting or withdrawing these devices.

With a conventional balloon dilatation catheter used, for example, for an angioplasty procedure, a relatively narrow cross-sectional catheter opening due to the relatively thick catheter sidewalls might be a nuisance but generally would not completely defeat the purpose of such a catheter. Such a device would still generally function as long as sufficient fluid could gradually be transferred through the catheter shaft in order to inflate the balloon and thereby dilate the blood vessel. By contrast, for a heat transfer catheter, the inability to establish and maintain a relatively high fluid flow rate through the catheter would completely defeat the purpose of continuously transferring controlled amounts of thermal energy to or away from remote internal body locations. A slow or uneven flow of heat transfer fluid through the catheter lumen would be unable to overcome the continuous heating or cooling effect of the surrounding body tissue along the relatively long length of the catheter. Moreover, if the heat transfer catheter was intended to be used in conjunction with a dilatation balloon, or with a guide wire, or with a medical instrument, a third, a fourth or additional catheter lumens would need to be provided, each defined by its own relatively thick sidewalls, thereby further restricting the already limited open, cross-sectional area.

Still another problem with the conventional thick-walled multi-lumen catheter is that the relatively thick sidewalls act as insulation and reduce heat transfer between any fluids inside and the surrounding body tissue. Yet another problem with the conventional thick-walled multi-lumen catheters is that the thick walls tend to be relatively rigid and thus do not closely conform to the surrounding body canal, thereby further reducing heat transfer.

These and other problems with and limitations of the prior art catheters in connection with heat transfer applications are overcome with the heat transfer catheters of this invention.

OBJECTS OF THE INVENTION

Accordingly, it is a general object of this invention to provide a catheter apparatus suitable for heat transfer applications inside a living body together with methods for making and using such apparatus.

A principal object of this invention is to provide a heat transfer catheter with fluid lumens having at least in part very thin, high strength sidewalls that are readily inflatable under fluid pressure and readily collapsible under vacuum.

It is also an object of this invention to provide a heat transfer catheter having fluid lumens with very thin, high strength sidewalls that have high heat transfer properties.

A further object of this invention is to provide a heat transfer catheter having fluid lumens with very thin, high strength sidewalls that, when inflated under fluid pressure, closely conform to the geometry of the surrounding body cavity.

A specific object of this invention is to provide a catheter apparatus capable of continuously transferring controlled amounts of thermal energy to or away from adjacent internal body locations that are relatively distant from the point of entry of the catheter into the body over an extended period of time.

Still another specific object of this invention is to provide a heat transfer balloon dilatation catheter capable of dilating a remote internal body location while simultaneously delivering controlled amounts of thermal energy to or withdrawing controlled amounts of thermal energy from an adjacent body location.

Yet another specific object of this invention is to provide a heat transfer catheter for enclosing a diagnostic or therapeutic instrument while simultaneously transferring controlled amounts of thermal energy to or away from all or a portion of the instrument.

These and other objects and advantages of this invention will be better understood from the following description, which is to be read together with the accompanying drawings.

SUMMARY OF THE INVENTION

The heat transfer catheter apparatus of the present invention comprises very thin-walled, high strength thermoplastic tubular material defining a plurality of lumens, at least two of which are adjacent and readily inflatable under fluid pressure and readily collapsible under vacuum. Fluid connection means are provided at or proximate to the distal ends of the two adjacent lumens to define a closed loop fluid containment and circulation system whereby heat transfer fluid from a first, inlet lumen is passed directly to a second, outlet lumen such that a continuous flow of heat transfer fluid through the two lumens can be established and maintained. In one specific embodiment of the present invention, the heat transfer catheter apparatus further comprises a heat transfer fluid, e.g., a cryogenic fluid, inside said inlet and outlet lumens, said fluid being maintained at a substantially constant temperature which is different from normal body temperature. For example, the heat transfer fluid may be at a temperature at least 10° C. different from that of the rest of the subject body. Another specific embodiment of the present invention comprises the step of monitoring the fluid temperature going into said inlet lumen and coming out of said outlet lumen. This embodiment may also comprise the step of adjusting the fluid flow rate through said catheter apparatus so that the fluid coming out of said outlet lumen is at substantially the same temperature as the fluid going into said inlet lumen. Using this method, the temperature of the fluid coming out of said outlet lumen may be maintained within 1° C. of the temperature of the fluid going into said inlet lumen.

BRIEF DESCRIPTION OF THE DRAWINGS

FIG. 1 is a schematic longitudinal sectional view of a heat transfer catheter apparatus according to one embodiment of the invention.

FIG. 2 is a cross-sectional view of the catheter apparatus of FIG. 1 along the line 2—2.

DETAILED DESCRIPTION OF THE INVENTION

Figure 3:
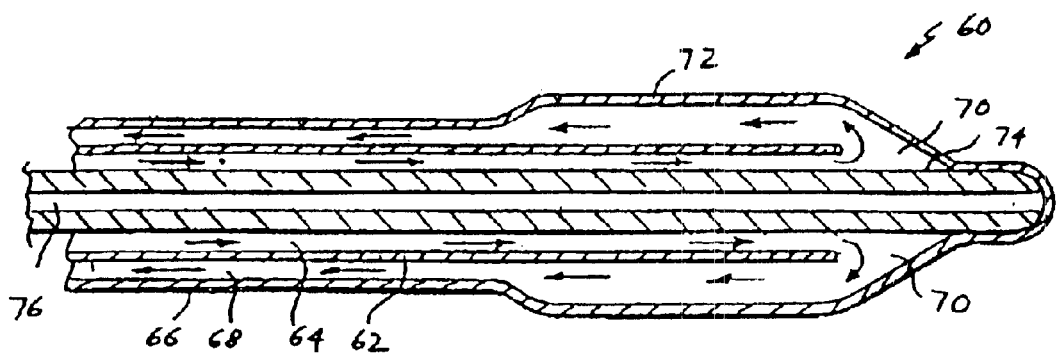
FIG. 3 is a schematic longitudinal sectional view of a heat transfer balloon dilatation catheter apparatus according to another embodiment of the invention.

In each of the drawings, as described below, it should be understood that the wall thicknesses of the catheter and balloon lumens have been greatly exaggerated relative to other elements and to other dimensions for purposes of illustration.

FIG. 1 shows a schematic longitudinal sectional view of a heat transfer catheter apparatus 10 according to the present invention comprising a substantially concentric, coaxial configuration of multiple lumens or channels. The concentric, coaxial arrangement of the multiple lumens can be better understood by reference to FIG. 2, a cross-sectional view taken along the line 2—2 of FIG. 1. Returning to FIG. 1, a first, inner catheter tube 12 defines a central conduit 11 receiving a guide wire 13. Catheter tube 12 may be of conventional, thick-walled construction or, alternatively, comprise very thin sidewalls. For purposes of this invention, the terms "very thin walls" or "very thin-walled" refer to elongated sleeves or catheters having sidewalls ranging in thickness from about 0.0002 inches up to about 0.002 inches, and, in some preferred embodiments, a wall thickness not exceeding 0.0009 inches. By comparison, the conventional "thick-walled" constructions of prior art multi-lumen catheters typically range in thickness from about 0.003 to about 0.010 inches or more. For purposes of this invention, the term "elongated" refers to catheter apparatus or to sleeves having an overall length-to diameter ratio of about 25:1 or greater. In the embodiment of FIG. 1, if catheter tube 12 is of conventional construction, tube 12 may provide sufficient rigidity by itself for insertion of the apparatus into a body canal or passageway. Alternatively, if inner catheter tube 12 is of very thin-walled construction, wire guide 13, previously positioned using a guide catheter or other conventional manner, may be needed in order to facilitate threading the catheter apparatus through a blood vessel or similarly narrow passageway. Inner catheter tube 12 may be of single or multi-lumen construction depending on the number of channels desired for a particular application. Catheter tube 12 may be configured open at both ends, for example to fit over a wire guide 13, and to act as a channel to inject or drain fluid, or to contain a diagnostic or therapeutic device. Alternatively, tube 12 can also be sealed at its distal end or configured in other advantageous ways.

Surrounding at least a portion of the length of inner catheter tube 12 is a very thin-walled, inflatable and collapsible, elongated inner sleeve 14 which may be, but need not be, at least partially sealed at its distal end to the outer surface of tube 12 so as to create a second or intermediate lumen 16 comprising an annual region with a donut-like cross section surrounding catheter tube 12. The annular configuration of lumen 16 can be better understood by reference to FIG. 2. For example, if tube 12 has an external diameter of about 0.04 inches, sleeve 14 may comprise biaxially-oriented polyethylene terephthalate (PET) and have an inner diameter of about 0.087 inches and a sidewall thickness of about 0.0005 inches. Surrounding at least a portion of the length of sleeve 14 is a very thin-walled, inflatable and collapsible, elongated outer sleeve 20 which is sealed at its distal end to the outer surface of tube 12 at a point distal from the distal end of sleeve 14 so as to create a third or outer lumen 22 comprising an annular region with a donut-like cross section surrounding sleeve 14. The annular configuration of lumen 22 can be better understood by reference to FIG. 2. In the preceding example, sleeve 20 may comprise biaxially-oriented PET and have an inner diameter of about 0.125 inches and a sidewall thickness of about 0.00065 inches. Fluid connection means 18, in this case comprising an opening between the open distal end of sleeve 14 and the inner wall of sleeve 20, places the distal end of lumen 16 in direct fluid communication with the distal end of lumen 22. Alternatively, the fluid connection means may comprise one or a plurality of apertures in the common wall means (i.e. in sleeve 14) separating lumens 16 and 22. In the foregoing example, the total cross-sectional area available for inlet and outlet fluid flow, as seen in FIG. 2, represents approximately 87% of the available cross-sectional area of the body canal in which the catheter apparatus is positioned. For the heat transfer catheters of this invention, at least about 60%, and preferably greater than about 80% of the available cross-sectional area of the body canal should be available for fluid flow. Although lumens 16 and 22 are shown in FIG. 1 as single lumens, it should be appreciated that one or both of these lumens may be fabricated as a multi-lumen structure, but obviously with some small associated loss of available fluid flow area because of additional wall means.

Catheter apparatus 10 as shown in FIG. 1 further comprises a first or proximal manifold section 30 and a second or distal manifold section 32. The distal end of manifold 30 is adapted to sealingly mate with the proximal end of manifold 32, for example by means of male and female threaded elements, 34 and 36 respectively, in combination with a resilient O-ring 38. Alternatively, manifolds 30 and 32 may be adhesively bonded to one another. Male element 34 of manifold 30 further comprises a centrally-located bore 40. Manifold 30 also comprises a fluid inlet port 42 connected to a source, such as reservoir 43, of fluid via a fluid fitting, which may also comprise an inlet valve 41 or other fluid flow control means, and an end seal 44. End seal 44 of manifold 30 also comprises a centrally-located bore 46. Bore 46 is sized so as to receive catheter tube 12. Fluid sealing means (not shown) are provided between the outside of tube 12 and the surface of bore 46 to prevent fluid leakage. Bore 40 is sized so as to receive both tube 12 and sleeve 14. The proximal end of sleeve 14 comprises fluid sealing means, such as an annular lip or flange 15 projecting radially outward and capable of being bonded or sealed to an inner wall of manifold 30. Alternatively, the outside of the proximal end of sleeve 14 may be adhesively bonded to the wall of bore 40.

Manifold 32 further comprises an outlet port 50, which may comprise an outlet valve 51 or other fluid flow control means, a tapered distal end 52 having a tubular projection 54, and a centrally-located opening 56 passing through tapered end 52 and projection 54. Opening 56 is sized so as to receive catheter tube 12 and sleeves 14 and 20 while leaving an open annular region defined by the outside of sleeve 14 and the inside surface of sleeve 20 through which fluid can pass. The outside of the proximal end of sleeve 20 may be adhesively bonded to the wall of opening 56. Thus, after the distal portion of catheter apparatus 10 is positioned in the body, fresh heat transfer fluid at a desired temperature, ordinarily (but not necessarily) different from normal body temperature, first enters manifold 30 through inlet port 42 (as illustrated by the fluid direction arrows), passes through the interior cavity of manifold 30 into the proximal end of sleeve 14 at lip 15, then passes through inlet fluid lumen 16 to the distal end of sleeve 14, then passes directly through fluid connection means 18 into outlet fluid lumen 22, then passes back through lumen 22 to the proximal end of sleeve 20, then passes into the interior of manifold 32 from which it exits through exit port 50. As used herein, the term "inlet fluid lumen" means a passageway or conduit of an elongated catheter through which fluid flow is substantially in a direction from the proximal end toward the distal end. Correspondingly, the term "outlet fluid lumen" means a passageway or conduit of a catheter through which fluid flow is substantially in a direction from the distal end toward the proximal end. The spent heat transfer fluid exiting through port 50 may be recovered and heated or cooled (as necessary), for example with a conventional heating or cooling jacket 45 surrounding fluid reservoir 43, to restore it to the desired temperature and then recycled back to inlet port 42.

The heat transfer fluids that are useful in the practice of this invention include both gases and liquids, but are preferably liquid. The fluid may be water or an aqueous solution, for example normal saline, provided the desired heating or cooling temperature is within the liquid range of water, i.e. about 0–100° C. For special applications, particularly for operating temperatures below 0° C. or above 100° C., other fluids, such as the various halogenated hydrocarbons (e.g. "Freon"), may be utilized. Obviously the selected fluid must be one that will be chemically compatible with the material from which the fluid lumens are constructed at the desired operating temperature.

As illustrated in FIG. 1, manifold sections 30 and 32 may comprise metal, plastic or other suitable materials. Catheter tube 12, inner sleeve 14 and outer sleeve 20 may comprise the same or different thermoplastic materials. The choice of materials and fabrication techniques may be adapted to meet particular design specifications or to realize particular properties of the completed apparatus. Some of the specific fabrication techniques, material selections, and desirable design features that are within the scope of this invention are presented below for purposes of illustration. Other advantageous variations will be apparent to those skilled in the art, and such obvious variations are also considered to be within the scope of this invention.

With regard to sleeves 14 and 20, it is preferred that these sleeves be of high tensile strength and able to withstand anticipated internal fluid operating pressures, which, for some applications, may be on the order of about 200 psi and higher, while, at the same time, being sufficiently thin-walled to have good heat transfer properties, to insure good contact with the walls of the internal body cavity during use, and to minimize wasted internal space. These sleeves should also be readily inflatable under fluid pressure and readily collapsible under vacuum to facilitate insertion and removal of the catheter apparatus. To realize these combined objectives, sleeves 14 and 20 should have sidewalls not exceeding a thickness of about 0.002 inches, preferably less than about 0.001 inches, and for some embodiments, less than 0.0009 inches. Sleeves 14 and 20 can be fabricated from an orientable polymeric material, for example using tubing extrusion and blow molding techniques, such as those taught in my U.S. Pat. Nos. 5,411,477 and 5,342,301. Biaxially-oriented PET sleeves can be prepared as thin as 0.0002 inches, for example, while retaining adequate tensile strength to insure against any ruptures while in use. Because thicker walls of biaxially-oriented PET tend to be somewhat rigid, it is preferred that such sleeves for this invention have sidewall thicknesses ranging from about 0.0002–0.0009 inches. In an alternative embodiment for certain applications, sleeves 14 and/or 20 may be fabricated from weaker but more flexible materials. For example, polyurethane sleeves may have sidewalls as thick as about 0.005 inches while still retaining the necessary flexibility for expansion, collapse, and conformity with the walls of the internal body cavity while in use. It will be understood that, for any given sleeve material, thinner sleeves will have better heat transfer properties than thicker sleeves.

For most applications, including all dilatation applications, it is preferred that fluid-carrying sleeves 14 and 20 be relatively inelastic. Fabrication of sleeves 14 and 20 from biaxially-oriented PET, as discussed above for example, would yield very thin-walled, high strength, relatively inelastic sleeves. Any polymeric material capable of being oriented in at least one direction with resultant enhancement of mechanical properties, particularly strength, could be used to fabricate one or more of the sleeves and catheters of this invention. Depending on the specific apparatus construction and intended application, such materials include PET, nylon, crosslinked polyethylene and ethylene copolymers, urethanes, vinyls, and Teflon, among others. In some applications, it may be preferred to fabricate outer sleeve 20, or both sleeves 14 and 20 from an elastomeric material. One such application would be where only relatively low fluid pressures are needed, for example where the catheter apparatus does not include a dilatation balloon and is not expected to be used in a dilatation procedure. Another such application would be where variations in internal anatomy would prevent an inelastic outer sleeve from making good heat transfer contact with the walls of the internal cavity or passageway.

If sleeves 14 and 20 are fabricated from PET, in addition to containing a heat transfer fluid in accordance with this invention these sleeves would also be capable of transmitting microwave energy, Nd:YAG laser energy, UV laser energy, and others from the proximal to the distal end of the apparatus. Also, if the fluid-carrying sleeves are fabricated from a suitable material, such as biaxially-oriented PET or PTFE (Teflon), the catheter apparatus would be capable of circulating cryogenic fluids for selective freezing of tissue such as cancerous tumors. In this case, for certain applications, it may be necessary to utilize multiple lumens so as to combine heating of the catheter via this technology along most of the length of the catheter while having the cryogenic freezing occur only at a specific desired location at or near the distal end of the catheter apparatus. The heating would prevent the entire catheter from freezing, thereby damaging tissue areas that should not be treated. For example, multiple lumens inside catheter tube 12 could be used to circulate a cryogenic fluid while sleeves 14 and 20 contained a heating fluid to insulate adjacent tissue along the length of the catheter except for the distal end beyond the end of sleeve 20. In still another embodiment, the distal end of tube 12 may communicate with a balloon element, which could then also provide heating or cooling effects. Simultaneous selective heating and cooling can also similarly be provided with the catheter apparatus according to this invention; or, differential heating or cooling can be provided where, for example, one side of the catheter is hotter or cooler than the other side in order to provide for treatment of asymmetric anatomical features. Alternative embodiments of the catheter apparatus, as hereinafter described, may also be adapted for such differential heating and/or cooling applications.

In still another embodiment of this invention, the diameters and wall thicknesses of tube 12 and of sleeves 14 and 20 may be selected such that lumens 16 and 22 have substantially equal cross-sectional areas for fluid flow. Alternatively, by adjusting the diameters of one or more of tube 12, sleeve 14 and sleeve 20, the cross-sectional areas of annular lumens 16 and 22 may be varied to create different pressure gradients and fluid flow rates. In another fabrication variation, sleeves 14 and 20 may be formed so as to have substantially constant cross-sectional diameters along their respective lengths at constant fluid pressure. Alternatively, one or both of sleeves 14 and 20 may be formed so as to have varying cross-sectional diameters along their lengths in order to generate particular flow patterns, for example to cause turbulent fluid flow at a desired location for purposes of increased heat transfer.

FIG. 3 is a schematic, cross-sectional view of an alternative embodiment of a heat transfer catheter in accordance with this invention. In FIG. 3, catheter apparatus 60 comprises a multi-lumen balloon dilatation catheter comprising a first or inner sleeve 62, defining an open space or inner lumen 64, and a second or outer sleeve 66 surrounding inner sleeve 62 so as to create an outer annular lumen 68. Inner sleeve 62 is formed open at its distal end and spaced from the inner wall of sleeve 66 so as to create a fluid connection 70. Outer sleeve 66 is formed closed at its distal end. The closed distal end of sleeve 66 is at a point that is distal from the open distal end of sleeve 62 so that fluid may pass through fluid connection means 70 from fluid inlet lumen 64 into fluid outlet lumen 68.

Proximate to its distal end, outer sleeve 66 comprises a dilatation balloon segment 72. Balloon segment 72 is preferably of very thin-wall, high strength construction, substantially inelastic, and readily inflatable under fluid pressure and readily collapsible under vacuum. In a preferred embodiment of this variant, at least sleeve 66 and balloon segment 72 comprise a unitary, integral and seamless unit wherein said sleeve portion and said balloon segment are integrally formed in accordance with the teachings of my U.S. Pat. No. 5,411,477. In this embodiment of the invention, fresh heat transfer fluid is introduced into the proximal end of inner lumen 64, passes through lumen 64 and fluid passage means 70 directly into outer lumen 68, through the interior of balloon segment 72, and then back along lumen 68 to the proximal end of the apparatus where the spent fluid is withdrawn. During use, fluid flow control means, such as inlet and outlet valves in conjunction with a manifold structure as shown in FIG. 1, at the proximal ends of lumens 64 and 68 may be used to maintain fluid pressure inside lumens 64 and 68 at a level that is sufficient to fully inflate balloon segment 72. Alternatively, a restriction can be incorporated into the manifold so as to create pressure in the lumens.

The heat transfer balloon dilatation catheter apparatus of FIG. 3 may be utilized in several different ways. In one embodiment, lumens 64 and 68 may be partially inflated with fluid in order to provide the stiffness needed to insert the catheter. Once the apparatus is properly positioned, the fluid pressure may be increased so as to fully inflate the dilatation balloon segment 72. Alternatively, a separate rod or hollow tube 74, as illustrated in FIG. 3, can be inserted through inner lumen 64 to provide stiffness. Tube 74 may be a solid rod or a hollow tube defining another lumen 76. Tube 74 may also comprise an elongated diagnostic or therapeutic device that is either permanently attached to the catheter apparatus or is removable, so that the catheter apparatus can be disposable and the medical instrument reusable or vice versa. Examples of instruments that could be utilized in such a combination catheter apparatus include microwave antennas, lasers, ultrasound probes, induction coils, and electric heating elements.

The requisite properties of sleeves 62 and 66 in FIG. 3, the materials from which these sleeves are prepared, and the sleeve fabrication techniques are similar to those discussed above for sleeves 14 and 20 respectively in FIG. 1. Thus, sleeves 62 and 66, including balloon segment 72, must have sufficient strength to withstand anticipated internal fluid operating pressures while, at the same time, being sufficiently thin-walled to have good heat transfer properties, to insure good contact with the walls of the internal body cavity during use, and to minimize wasted internal space. These sleeves should also be readily inflatable under fluid pressure and readily collapsible under vacuum. To realize these combined objectives, sleeves 62 and 66, including balloon segment 72, generally have sidewalls not exceeding a thickness of about 0.002 inches. Similar to sleeves 14 and 20 in FIG. 1, sleeves 62 and 66 in FIG. 3 may be fabricated from an orientable polymeric material, for example using tubing extrusion and blow molding techniques. For this embodiment of the invention, sleeves 62 and 66 and, particularly, balloon segment 72, should be relatively inelastic such that, when fully inflated and undeformed, balloon segment 72 dilates to a predetermined, repeatable size and shape. Biaxially-oriented PET sleeves having sidewall thicknesses of about 0.0002–0.0009 inches are a particularly advantageous embodiment of this version of the invention.

The heat transfer balloon dilatation catheter apparatus as described above may further comprise one or a plurality of adjacent lumens located externally of the maximum realizable dimension of the inelastic balloon segment 72 and adjacent to the wall of the balloon when the balloon is fully inflated and undeformed. In this embodiment, the balloon segment shares with each said adjacent, external lumen a single-layer, integrally formed wall section comprising a portion of the balloon wall and separating the interior of the balloon from the interior of the adjacent, external lumen. The balloon comprises a very thin, flexible, high strength, substantially inelastic material having a wall thickness of less than about 0.0015 inches, preferably less than about 0.0009 inches. The preparation and use of such multi-lumen balloon dilatation catheters is taught in my U.S. Pat. No. 5,342,301.

Figure 4:
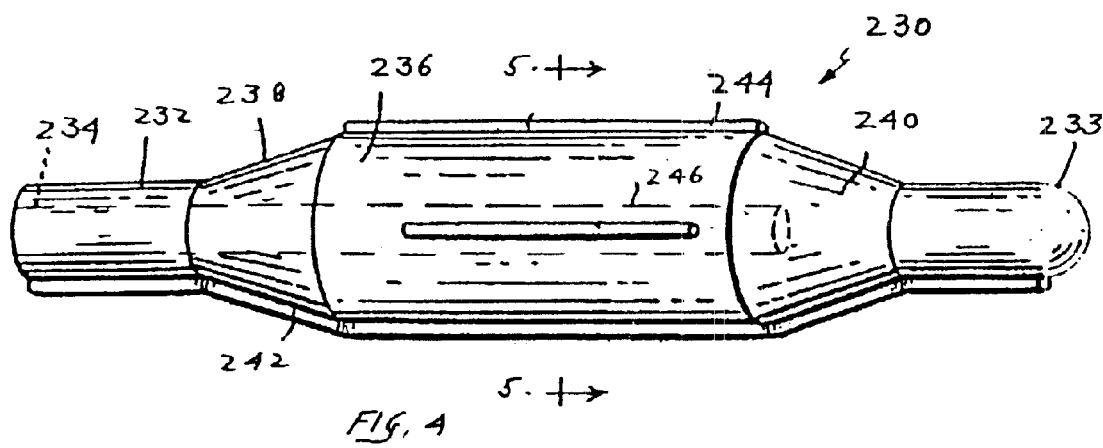
FIG. 4 is an isometric view of a heat transfer balloon dilatation catheter apparatus similar to FIG. 3 but also comprising three straight, perimetrical lumens adjacent to the balloon wall.
Figure 5:
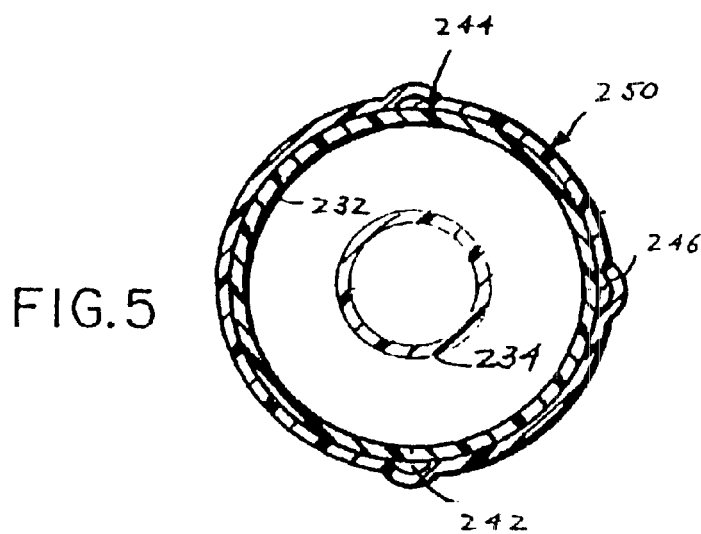
FIG. 5 is a cross-sectional view of the catheter apparatus of FIG. 4 along the line 5—5.
Figure 6:
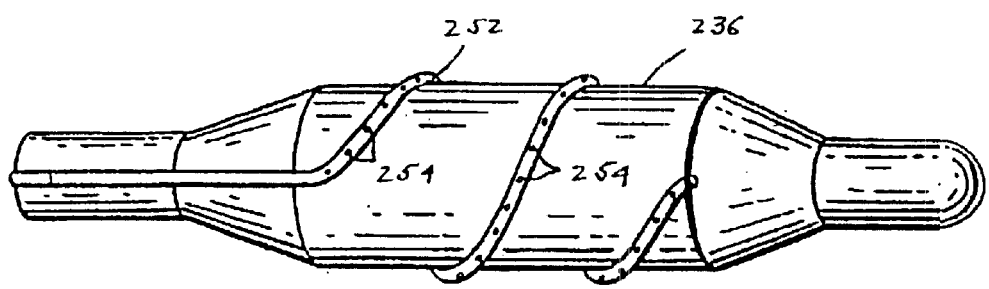
FIG. 6 is an isometric view of a heat transfer balloon dilatation catheter apparatus similar to FIG. 3 but also comprising a helical, perimetrical lumen having pin holes for delivering fluid to a body cavity.

FIGS. 4–6 illustrate one set of embodiments of a heat transfer, multi-lumen balloon dilation catheter apparatus according to the present invention. FIG. 4 shows a previously-formed heat transfer balloon dilatation catheter apparatus 230, generally comparable to apparatus 60 of FIG. 3, comprising an outer sleeve 232 (best seen in FIG. 5) having a closed distal end 233 and a concentric, coaxial inner sleeve 234. This structure is clearly evident in FIG. 5, a cross-sectional view along the line 5—5 of FIG. 4. Outer sleeve 232 comprises a balloon segment 236 having conical or tapered ends 238 and 240. Thus, in one embodiment in accordance with this invention, the catheter apparatus of FIG. 4 can be operated as a heat transfer catheter comparable to FIG. 3, wherein heat transfer fluid enters through the lumen defined by inner sleeve 234, dilates balloon segment 236, and exits through the annular lumen defined between sleeves 232 and 234, with fluid flow controlled by inlet and outlet valves in conjunction with a manifold structure as shown in FIG. 1. Other embodiments utilizing the apparatus of FIG. 4, as discussed below, are also contemplated, however. In accordance with the technique described in U.S. Pat. No. 5,342,301, mandrels or forming wires may be positioned along the external surface of outer sleeve 232 and a tube 250 (best seen in FIG. 5) of a heat-shrinkable thermoplastic thereafter shrunk around sleeve 232 so as to create one or more of adjacent, external lumens 242, 244, and 246, each integrally formed with a portion of sleeve 232.

Fluid flow connection means, for example one or more apertures, may be provided in the integrally formed wall means that separates the interior of balloon segment 236 and one or more of the adjacent, external lumens 242, 244 and 246. In this embodiment, instead of having coaxial inner sleeve 234, fluid may be supplied to balloon segment 236 through sleeve 232 and withdrawn through an externally-extending adjacent, external lumen such as lumen 242. As seen in FIG. 4, external, adjacent lumen 242 can be formed so as to run the entire length of sleeve 232, including balloon segment 236 and conical ends 238 and 240. Thus, in still another embodiment of this invention, an apparatus similar to that shown in FIG. 4 but having two perimetrical lumens like lumen 242 running the entire length of sleeve 232 could be used to deliver heat transfer fluid to a body location distal of balloon segment 236. The flow of heat transfer fluid, in through one of said perimetrical lumens and out through the other, would not be significantly interrupted even during dilatation of balloon segment 236. Similarly, and for other applications, external, adjacent lumen 244 can be formed so as to run from one end of the middle or working section of balloon 236 to the other. Similarly, external, adjacent lumen 246 can be formed so as to begin and end within the working section of balloon 236. By proper selection of the forming wires, external, adjacent lumens can be created of the same or different diameters, of uniform or non-uniform cross-section, and of circular or other cross-sectional shape, as desired for particular applications. Employing a similar preparation technique, a heat transfer balloon dilatation catheter apparatus can be prepared as shown in FIG. 6 wherein an external, adjacent lumen 252 runs in a helical pattern around the outside wall of balloon 236. Helical lumen 252 may comprise, in one embodiment, a plurality of pinholes 254 along its length to precisely deliver medication or other fluids to select body locations.

Figure 7:
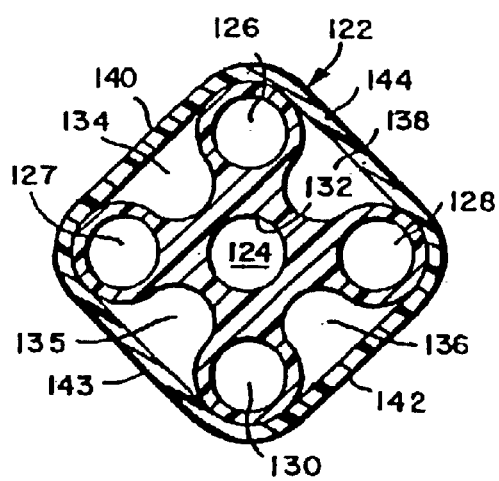
FIG. 7 is a cross-sectional view of the balloon portion of another type of multi-lumen heat transfer balloon dilatation catheter apparatus according to another embodiment of this invention.
Figure 8:
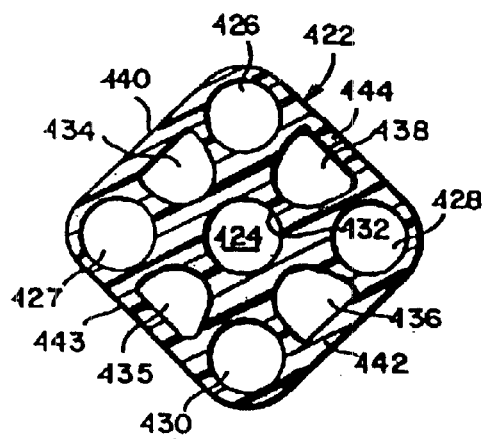
FIG. 8 is a cross-sectional view of the balloon portion of still another type of multi-lumen heat transfer balloon dilatation catheter apparatus according to the present invention.

FIGS. 7 and 8 illustrate alternative embodiments of a heat transfer, multi-lumen balloon dilatation catheter apparatus according to the present invention. The preparation and use of multi-lumen balloons having cross-sectional configurations similar to those shown in FIGS. 7 and 8 is also taught in my U.S. Pat. No. 5,342,301. Thus, the nine-lumen balloon structure of FIG. 7 is prepared either by heat-shrinking a thermoplastic sleeve over the four-lobe interior structure (which, in turn, is made by blow molding a five-lumen extruded preform) or by blow molding a five-lumen extruded preform inside a thermoplastic sleeve.

FIG. 7 shows a multi-lumen balloon 122 in accordance with this alternative embodiment of the present invention. In this design, the catheter shaft 124 is of a conventional design, except that it does not have to be provided with lumens for allowing for fluid flow when the balloon is inflated. Instead the balloon is formed as a multi-lumen balloon in accordance with my U.S. Pat. No. 5,342,301 for providing the necessary fluid flow, and for providing the necessary inflation so as to achieve dilatation of a selected body passageway. As seen in FIG. 7, center lumen 132 receives the catheter shaft 124 so that the balloon can be secured in place with a suitable adhesive to the shaft. At least four lumens 126, 127, 128 and 130 are radially spaced around center lumen 132 for receiving the pressurized fluid for inflating each of these lumens so as to achieve dilatation. The lumens 126, 127, 128 and 130, must be closed or connected and be adapted to be in fluid communication with a source of pressurized fluid. Lumens 134, 135, 136 and 138, are formed within the spaces between lumens 126, 127, 128 and 130, and the corresponding wall sections 140, 143, 142 and 144, when lumens 126, 127, 128 and 130 are inflated.

In FIG. 7, one or more of lumens 126, 127, 128 and 130, for example, could be utilized as inlet lumens for heat transfer fluid, and one or more of lumens 134, 135, 136 and 138 could be utilized as outlet lumens for heat transfer fluid, by providing fluid connection means between adjacent inlet and outlet lumens. For example, lumen 126 could be provided with apertures in its sidewall to permit fluid flow into one or both of adjacent lumens 134 and 138. Correspondingly, lumen 130 could be provided with apertures in its sidewall to permit fluid flow into one or both of adjacent lumens 135 and 136. In this example, inlet lumen 126 and outlet lumens 134 and 138 could carry heat transfer fluid at a first temperature, while inlet lumen 130 and outlet lumens 135 and 136 could carry heat transfer fluid at a second, different temperature. Those lumens not being utilized to circulate heat transfer fluid, such as central lumen 132 and side lumens 127 and 128 in the above example, could be utilized to enclose a medical instrument, a guide wire, or the like, or to provide fluid passageways for medicine delivery, fluid drainage, or perfusion applications. Although FIG. 7 illustrates a multi-lumen dilatation balloon having nine lumens, at least two of which must be interconnected to provide fluid flow in accordance with the present invention, it will be understood that similar preparation techniques could be used to prepare similar multi-lumen balloon structures having more or fewer lumens than nine.

The structure of FIG. 8 is prepared by blow molding a nine-lumen extruded preform of appropriate starting geometry, also as described in U.S. Pat. No. 5,342,301. Similar to FIG. 7, FIG. 8 illustrates a nine-lumen balloon structure in which one or more of lumens 426, 427, 428 and 430, for example, could be utilized as inlet lumens for heat transfer fluid, and one or more of lumens 434, 435, 436 and 438 could be utilized as outlet lumens for heat transfer fluid, by providing fluid connection means between adjacent inlet and outlet lumens. In FIG. 8, reference numerals 422, 424, 432, 440, 442, 443 and 444 refer respectively to the comparable structural elements as in FIG. 7, namely reference numerals 422/122 (multi-lumen balloon); 424/124 (catheter shaft); 432/132 (center lumen); and 440/140, 442/142, 443/143, and 444/144 (wall sections). For example, lumen 427 could be provided with apertures in its sidewall to permit fluid flow into one or both of adjacent lumens 434 and 435. Correspondingly, lumen 428 could be provided with apertures in its sidewall to permit fluid flow into one or both of adjacent lumens 436 and 438. In this example, inlet lumen 427 and outlet lumens 434 and 435 could carry heat transfer fluid at a first temperature, while inlet lumen 428 and outlet lumens 436 and 438 could carry heat transfer fluid at a second, different temperature. As discussed above with respect to FIG. 7, those lumens not being utilized to circulate heat transfer could be utilized for other applications. It will be understood that similar preparation techniques could be used to prepare similar multi-lumen balloon structures having more or fewer lumens than nine.

Figure 9:
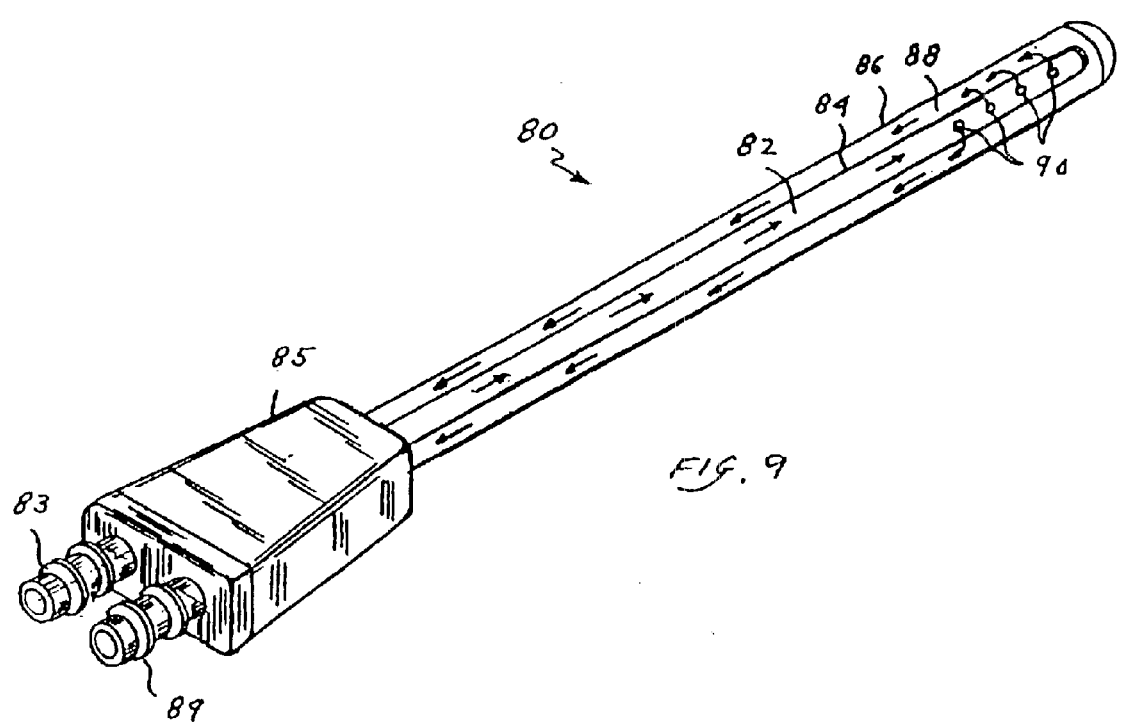
FIG. 9 is a schematic, isometric, partial cross-sectional view of a heat transfer catheter according to still another embodiment of the invention.

FIG. 9 illustrates yet another embodiment of this invention. In FIG. 9, catheter apparatus 80 comprises two concentric, coaxial lumens consisting of an inner inlet lumen and an outer outlet lumen. The inner inlet lumen 82 defined by inner sleeve 84 is surrounded by a closed-end outer sleeve 86 of larger diameter than inner sleeve 84 thereby defining an annular outlet lumen 88 having a donut-like cross section. Inner sleeve 84 includes fluid communication means, such as multiple apertures or side holes 90 which permit fluid to pass directly from inlet lumen 82 to outlet lumen 88 at or near the distal end of inlet lumen 82. The proximal end of inlet lumen 82 is coupled to fluid inlet means 83, for example a one-way valve. Correspondingly, the proximal end of outlet lumen 88 is coupled to fluid outlet means 89, for example a one-way valve. Housing means 85 may be provided to facilitate coupling the inlet and outlet lumens to their respective inlet and outlet valves.

Similar to the embodiment shown in FIG. 3, the catheter apparatus of FIG. 9 may be filled with fluid and pressurized in order to stiffen it sufficiently to facilitate insertion or, alternatively, a solid rod or hollow tube (not shown) can be inserted into one of the lumens to provide the necessary stiffness. Instead of a rod or tube, an elongated diagnostic or therapeutic device may be used to provide stiffness. Such device may either be permanently attached to the catheter apparatus or it may be removable, so that the catheter apparatus can be disposable and the medical device reusable or vice versa.

FIGS. 1–6 and 9 as discussed above illustrate embodiments of this invention in which the heat transfer fluid inlet and outlet lumens are concentric and coaxial. This configuration is relatively easy to manufacture and generally permits maximum fluid flow for any given external catheter diameter because a single-layer wall means (for example, sleeve 14 in FIGS. 1 and 2, sleeve 62 in FIG. 3, sleeve 234 in FIG. 5, and sleeve 84 in FIG. 9) can serve as both the outer wall of an inner inlet lumen and as the inner wall of an outer, annular-shaped outlet lumen. Other configurations of inlet and outlet lumens, however, are also within the scope of this invention. FIGS. 7 and 8 illustrate two embodiments wherein the inlet and outlet lumens are not in a concentric, coaxial configuration. Another such alternative configuration is illustrated in FIG. 10.

Figure 10:
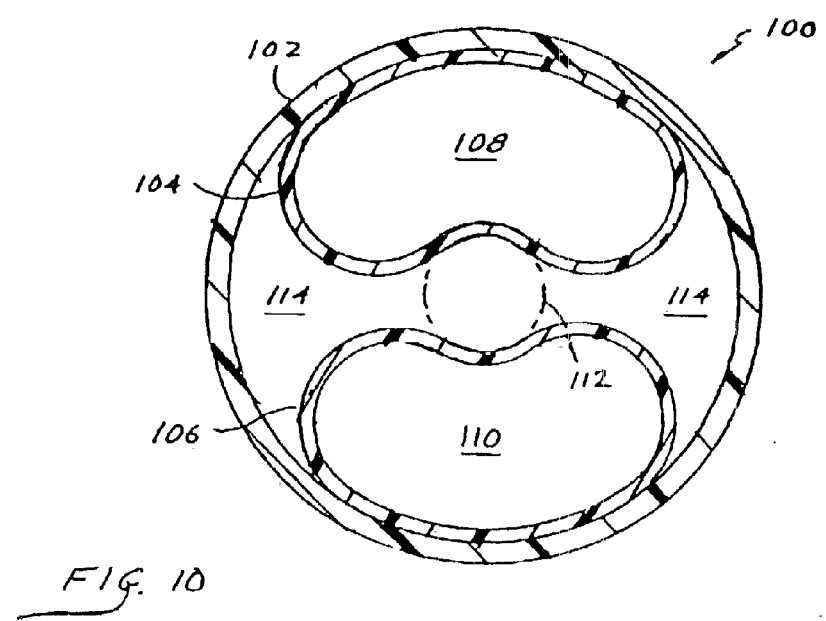
FIG. 10 is a schematic cross-sectional view of a heat transfer catheter according to yet another embodiment of the invention.

FIG. 10 is a schematic cross-sectional view of a different lumen configuration for another heat transfer catheter 100 in accordance with this invention. In FIG. 10, outer sleeve 102 surrounds and encloses two inner sleeves 104 and 106 of smaller diameter which define respectively lumens 108 and 110. Also shown in FIG. 10, enclosed within outer sleeve 102 but external of lumens 108 and 110, is a central longitudinal member 112 which may, in alternative embodiments, comprise a rod, a hollow tube, or a diagnostic or therapeutic instrument, or a combination of one or more. If, as illustrated in FIG. 10, sleeves 104 and 106 and member 112 are of such size and geometry as to not fill all of the interior space enclosed by outer sleeve 102, upon fluid inflation an irregularly shaped lumen 114 would also be created inside sleeve 102. Thus, in this embodiment, lumens 108 and 110 could be utilized as fluid inlet lumens for introducing heat transfer fluid to catheter apparatus 100, and lumen 114 utilized as the fluid outlet lumen. Fluid connection means (not shown), such as holes or apertures in sleeves 104 and 106, are provided to establish a flow of the heat exchange fluid from inlet lumens 108 and 110 to outlet lumen 114.

The catheter configuration illustrated in FIG. 10 facilitates a number of advantageous variations on the basic invention. For example, the catheter apparatus 100 of FIG. 10 can, similar to the embodiments of FIGS. 7 and 8, provide heat transfer fluid at two different temperatures, for example one for selective heating, the other for selective cooling. Different fluid flow rates can also be established in inlet lumens 108 and 110. Inner sleeves 104 and 106 may be either of the same or different diameters, wall thicknesses, and materials. By making one of the inner sleeves of a larger diameter than the other, upon fluid inflation member 112 will be displaced off-center and moved closer to one side of the inner wall of sleeve 102 than the other side. This embodiment may be useful where member 112 is a medical instrument. A similar result could be achieved by selectively inflating only one of the two inner sleeves 104 and 106.

It will be understood that a catheter apparatus according to this invention as illustrated in FIG. 10 could be prepared with only one inner sleeve (i.e. only one fluid inlet lumen) or, alternatively, with three, four or more inner sleeves instead of the two shown. It will also be understood that for any of the catheter apparatuses within the scope of this invention the heat transfer inlet and outlet lumens can be configured to run substantially the entire working length of the catheter or to occupy only a discrete, predetermined portion of the catheter. For example, the heat transfer inlet and outlet lumens may commence at the point where the catheter enters the body and terminate at a location intermediate of the distal end of the catheter. Alternatively, the heat transfer inlet and outlet lumens may be defined by conventional "thick-walled" sidewalls along a proximal section of the catheter, and defined by very thin sidewalls of about 0.0002–0.002 inches thickness only along a distal section of the catheter. In this construction, heat transfer would be minimized along the proximal, thick-walled section of the catheter and maximized at the thin-walled distal end.

Since certain changes may be made in the above-described apparatuses and processes without departing from the scope of the invention herein involved, it is intended that all matter contained in the above description shall be interpreted in an illustrative and not in a limiting sense.

Having described the invention, what is claimed is:

1. A heat transfer catheter apparatus, comprising:
   (a) a substantially elongate shaft;
   (b) at least one first lumen internal to said substantially elongate shaft, said at least one internal lumen configured:
      (i) to circulate a working fluid;
      (ii) to inflate under pressure of said working fluid; and
      (iii) to collapse under vacuum; and
   (c) a second lumen external and adjacent to said substantially elongate shaft, said second lumen having a spiral shape.

2. The catheter apparatus of claim 1;
   (a) further comprising a working heat transfer fluid supply; wherein
   (b) said working heat transfer fluid is saline.

3. The catheter apparatus of claim 1, further comprising a wire disposed within said first lumen.

4. The catheter apparatus of claim 1;
   (a) further comprising a working heat transfer fluid supply; wherein
   (b) said working heat transfer fluid supply circulates said working heat transfer fluid.

5. The catheter apparatus of claim 4, wherein said working heat transfer fluid supply is adapted to be operated to produce a pressurized working heat transfer fluid at a temperature above or below normal body temperatures.

6. The catheter apparatus of claim 1;
   (a) further comprising a working heat transfer fluid supply; wherein
   (b) the working fluid is an aqueous solution.

7. The catheter apparatus of claim 1, wherein said substantially elongate shaft is substantially straight.

8. The catheter apparatus of claim 1, wherein said second lumen helically encircles said substantially elongate shaft.

9. The catheter apparatus of claim 8, wherein:
   (a) said substantially elongate shaft is cylindrical and
   (b) said helical shape of said second lumen is tapered when said first lumen is inflated.

10. The catheter apparatus of claim 1, wherein said substantially elongate shaft is cylindrical and has an overall length-to-diameter ratio of 25:1 or greater.

* * * * *